US008920843B2

(12) United States Patent
Sawan et al.

(10) Patent No.: US 8,920,843 B2
(45) Date of Patent: Dec. 30, 2014

(54) SLOW RELEASE OF ORGANIC SALTS OF LOCAL ANESTHETICS FOR PAIN RELIEF

(75) Inventors: Samuel P. Sawan, Tyngsboro, MA (US); Daniel Jacobs, Mountain View, CA (US); Tadmor Shalon, Palo Alto, CA (US)

(73) Assignee: SVIP5 LLC, Palo-Alto, CA (US)

( * ) Notice: Subject to any disclaimer, the term of this patent is extended or adjusted under 35 U.S.C. 154(b) by 135 days.

(21) Appl. No.: 12/734,520

(22) PCT Filed: Nov. 7, 2008

(86) PCT No.: PCT/US2008/012617
§ 371 (c)(1),
(2), (4) Date: May 6, 2010

(87) PCT Pub. No.: WO2009/061497
PCT Pub. Date: May 14, 2009

(65) Prior Publication Data
US 2010/0233271 A1 Sep. 16, 2010

Related U.S. Application Data

(60) Provisional application No. 60/996,243, filed on Nov. 7, 2007.

(51) Int. Cl.
*A61K 9/14* (2006.01)
*A61K 31/445* (2006.01)
*A61P 17/02* (2006.01)
*A61P 23/02* (2006.01)
*A61K 9/10* (2006.01)
*A61L 26/00* (2006.01)
*A61K 9/06* (2006.01)
*A61K 9/00* (2006.01)
*A61K 31/167* (2006.01)
*A61K 9/12* (2006.01)

(52) U.S. Cl.
CPC ......... *A61L 26/0066* (2013.01); *A61L 2300/21* (2013.01); *A61K 9/10* (2013.01); *A61L 26/0076* (2013.01); *A61K 9/06* (2013.01); *A61K 31/445* (2013.01); *A61L 2300/622* (2013.01); *A61K 9/0024* (2013.01); *A61K 31/167* (2013.01); *A61L 2300/402* (2013.01); *A61K 9/0014* (2013.01); *A61K 9/12* (2013.01)
USPC .......................................... 424/489; 514/354

(58) Field of Classification Search
USPC ....................................................... 424/489
See application file for complete search history.

(56) References Cited

U.S. PATENT DOCUMENTS

| | | | |
|---|---|---|---|
| 3,949,071 A | 4/1976 | Alnor | |
| 4,168,308 A * | 9/1979 | Wretlind et al. | 514/221 |
| 4,492,685 A | 1/1985 | Keith et al. | |
| 4,828,832 A * | 5/1989 | De Cuellar et al. | 424/618 |
| 5,227,165 A * | 7/1993 | Domb et al. | 424/450 |
| 5,292,512 A | 3/1994 | Schaefer et al. | |
| 5,446,063 A * | 8/1995 | Reuter et al. | 514/535 |
| 5,635,205 A | 6/1997 | Nyqvist et al. | |
| 5,660,817 A * | 8/1997 | Masterman et al. | 424/49 |
| 5,670,524 A | 9/1997 | Eek | |
| 5,810,786 A | 9/1998 | Jackson et al. | |
| 5,814,659 A | 9/1998 | Elden | |
| 5,834,489 A | 11/1998 | Eek | |
| 5,912,271 A | 6/1999 | Brodin et al. | |
| 6,086,863 A | 7/2000 | Ritter et al. | |
| 6,217,911 B1 | 4/2001 | Vaugn et al. | |
| 6,238,702 B1 | 5/2001 | Berde et al. | |
| 6,255,502 B1 | 7/2001 | Penkler et al. | |
| 6,391,888 B1 | 5/2002 | Gleich | |
| 6,426,339 B1 | 7/2002 | Berde et al. | |
| 6,429,228 B1 | 8/2002 | Inagi et al. | |
| 6,495,602 B1 | 12/2002 | Bhagwat et al. | |
| 6,514,516 B1 | 2/2003 | Chasin et al. | |
| 6,521,259 B1 | 2/2003 | Chasin et al. | |
| 6,534,081 B2 | 3/2003 | Goldenheim et al. | |
| 6,645,521 B2 | 11/2003 | Cassel | |
| 6,699,908 B2 | 3/2004 | Sackler et al. | |
| 6,750,291 B2 | 6/2004 | Kim et al. | |
| 6,887,487 B2 | 5/2005 | Murthy et al. | |
| 6,946,137 B2 * | 9/2005 | Murthy et al. | 424/400 |
| 7,033,599 B2 | 4/2006 | Murthy et al. | |
| 7,166,641 B2 | 1/2007 | Lee et al. | |
| 2002/0045668 A1 * | 4/2002 | Dang et al. | 514/649 |
| 2002/0156101 A1 | 10/2002 | Isacsson et al. | |
| 2003/0027833 A1 | 2/2003 | Cleary et al. | |

(Continued)

FOREIGN PATENT DOCUMENTS

EP 2128123 A1 12/2009
WO 2005009408 A2 2/2005

OTHER PUBLICATIONS

Maruyama et al., "Sore throat and hoarseness after total intravenous anaesthesia," British Journal of Anaesthesia, 92(4):541-543, 2004.
Polglase, et al., "Continuous Wound Infusion of Local Anesthetic for the Control of Pain After Elective Abdominal Colorectal Surgery," Disease of the Colon & Rectum, 50:2158-2167, 2007.
Larsen, et al., "Diflunisal salts of bupivacaine, lidocaine and morphine use of the common ion effect for prolonging the release of bupivacaine from mixed salt suspensions in an in vitro dialysis model," European Journal of Pharmaceutical Sciences, 31:172-179, 2007.
Ostergaard, et al., "Bupivacaine salts of diflunisal and other aromatic hydroxycarboxylic acids: Aqueous solubility and release characteristics from solutions and suspensions using a rotating dialysis cell model," European Journal of Pharmaceutical Sciences, 26:280-287, 2005.

(Continued)

*Primary Examiner* — Audrea Buckley
(74) *Attorney, Agent, or Firm* — Edgar W. Harlan; Carolyn S. Elmore, Esq.; Elmore Patent Law Group, P.C.

(57) ABSTRACT

Particles of an organic acid salt of an amino acid amide or ester local anesthetic are employed as agents for the improved alleviation of pain. Particularly, the particles find use with surgically created wounds, where the particles may be administered directly into the bed of the wound or topically for transdermal transport.

20 Claims, 3 Drawing Sheets

(56) References Cited

U.S. PATENT DOCUMENTS

| | | |
|---|---|---|
| 2004/0058994 A1 | 3/2004 | Cassel |
| 2004/0076671 A1 | 4/2004 | Tippett |
| 2004/0214215 A1 | 10/2004 | Yu et al. |
| 2004/0228884 A1 | 11/2004 | Gupta |
| 2005/0002996 A1 | 1/2005 | Sojka et al. |
| 2005/0075296 A1 | 4/2005 | Murthy et al. |
| 2005/0255150 A1* | 11/2005 | Cassel et al. .................. 424/449 |
| 2006/0222687 A1 | 10/2006 | Carter et al. |
| 2006/0280801 A1 | 12/2006 | Kronenthal |
| 2007/0141162 A1 | 6/2007 | Murthy et al. |

OTHER PUBLICATIONS

Pietkiewicz, et al., "The expulsion of lipophilic drugs from the cores of solid lipid microspheres in diluted suspensions and in concentrates," International Journal of Pharmaceuticals, 310(1-2):64-71, 2006.

Nash, et al., "The Possibility of Lidocaine Ion Pair Absorption Through Excised Hairless Mouse Skin," Skin Pharmacol, 5(3):160-170, 1992.

Bica, et al., "Liqud forms of pharmaceutcal co-crystals: exploring the boundares of salt formaton," Royal Socey of Chemisty, 47(8):2267-2269, 2011.

* cited by examiner

SLOW RELEASE OF ORGANIC SALTS OF LOCAL ANESTHETICS FOR PAIN RELIEF

CROSS-REFERENCE TO RELATED APPLICATIONS

This application is a §371 filing from PCT/US2008/012617, filed Nov. 7, 2008, and claims the benefit under 35 U.S.C. §119(e)(1) of U.S. Provisional Application No. 60/996,243 filed Nov. 7, 2007, which applications are incorporated herein by reference in their entireties and from which applications priority is claimed pursuant to the provisions of 35 U.S.C. §§119/120.

BACKGROUND OF THE INVENTION

1. Technical Field

The field of this invention is the treatment of pain, particularly surgically caused or other type of wound.

2. Background of the Invention

In the management of post-operative pain, several kinds of drugs are widely used, amongst them local anesthetics and systemic opioids. Local anesthetics reversibly block the impulse conduction along nerves and other excitable membranes that primarily utilize sodium channels. Clinically, this action blocks sensation from specific areas of the body.

Surgery, whether by invasive procedures, e.g. resection, laparoscopy, or other operation resulting in penetration of the outer surface of a body part with the involvement of nerves, frequently leads to pain. With a growing emphasis on rapid return to function and out-patient surgery, the management of post-operative pain is receiving ever greater emphasis. Local anesthetics have found extensive use, but are usually short lived. Local anesthetic pumps and catheters are cumbersome and can suffer from inadequate distribution throughout the wound. In order to diminish post-operative pain, pain-killing medications, usually opioids, are prescribed. These untargeted medications affect all of the body, while only the portion involved surgically requires treatment. Other affected body systems are typically impacted adversely such as in constipation, nausea, respiratory depression, sedation, and confusion. It is therefore of great importance that methods be found to control surgical pain for extended periods of time at the site of surgery while minimizing the adverse impact on other bodily functions.

Local anesthetics of the "caine" family are weak bases. (By "caine" is intended anesthetics that end in the suffix caine, which will usually include amino acid amides and esters.) One of the classes of anesthetics that are amine bases also includes an aromatic ring, for example, a meta-xylyl group and an amide or ester functionality. The aromatic group with the other entities results in hydrophobicity, so that the members of the class are frequently employed as their hydrochloride salts to allow for water solubility. Examples of such anesthetics of the caine family include lidocaine (lignocaine), procaine, bupivacaine, ropivacaine, butacaine oxybuprocaine mepivacaine, prilocaine, amylocaine chloroprocaine, etidocaine, propoxycaine and tropacocaine. Local anesthetics are usually administered by injection into the area of the nerve fibers to be blocked. Thus, absorption and distribution are not as important in controlling the onset of effect as in determining the rate of offset of anesthesia and the likelihood of central nervous system and cardiac toxicity. Topical application of local anesthetics, where there is an intact skin barrier requires drug diffusion for both onset and offset of anesthetic effect. Therefore, the solubility and stability of the drug become major factors in determining the therapeutic effects of the drug. (Miller & Hondeghem, (1995), "Local Anesthetics" in Basic & Clinical Pharmacology, 6.sup.th Edition, Ed. by Katzung).

Among the local anesthetics, lidocaine, 2-(diethylamino)-N-(2,6-dimethylphenyl)-acetamide, in addition to its widespread use as a local anesthetic, is particularly known for its treatment of ventricular tachycardia (an arrythmia of the heart) as an intravenous injection solution. (See e.g., U.S. Pat. No. 3,968,205). Lidocaine is also used with vasoconstrictors to reduce regional blood flow in topical applications or aerosols (such as nasal aerosols to reduce nasal congestion). (See for example, U.S. Pat. No. 5,534,242). [In addition, lidocaine is known for its therapeutic effects in reducing post-herpetic neuralgia (PHN) nerve injury pain from shingles (herpes zoster and post herpetic neuralgia) and analogous neuropathies. For example, U.S. Pat. No. Re 37,727 discloses methods employing lidocaine intradermal administration by transport of lidocaine from the skin surface, using patches and dressings, into the skin.

Lidocaine base is freely lipid soluble. It is insoluble in water and thus not suitable for use in an aqueous solution, requiring ethanol or the like to obtain a liquid solution. However, its salt form, lidocaine-HCl, is very soluble in water and alcohol. Thus, lidocaine-HCl is the form that is used for preparation of injection solutions. However, for transdermal administration the hydrophilicity of the lidocaine hydrochloride salt inhibits transport across the skin. Furthermore, the action of the lidocaine salt can be short-lived, requiring repeated administrations to relieve the patient.

Other members of the caine family that have found extensive use are bupivacaine and ropivacaine, which find numerous studies in the scientific literature and references in the patent literature. For bupivacaine, see, for example, U.S. Pat. Nos. 6,699,908, 6,534,081, 6,521,259, 6,514,516, and 6,391,888, while in the scientific literature, Lambert et al. 2007 Arthritis Rheum 56, 2278-87; Ostergaard et al 2005 Eur J Pharm Sci 76, 280-7; and Larsen et al 2007 Eur J Pharm Sci 31, 172-9, as indicative of some of the activity in the field. Similarly, for ropivacaine, see, for example, U.S. Pat. Nos. 5,670,524, 5,834,489 and 2002/0156101, while in the scientific literature, see Polglase, et al 2007 Dis Colon Rectum, ePublication 10/3; Bariskaner, et al 2007 Methods Find Exp Clin Pharmacol 29, 337-11 and Brodner, et al 2007 Anesth Analg 105, 256-62. These anesthetics have been extensively reported in the manner in which they are administered, the particular context in which they are used and the companion drugs that are employed.

For slow release, extended anesthetic effects, and maintaining localized administration and/or minimizing toxicity, two different approaches have been employed, either individually or in combination, using a polymeric matrix or adjunctive compounds that extend the effective lifetime of the anesthetic. Neither of these approaches has proven to be entirely satisfactory in a medical setting due to the persistence of the polymeric matrix in the healing wound region and the difficulty of applying injectable formulations to broad surface and sub-surface areas of innervation associated with the surgical site. A simple effective method for providing extended pain relief is needed.

Examples of patents and patent applications that use polymeric matrices include U.S. Pat. No. 6,750,291 (Transdermal agent, film forming polyurethane and addition polymer); U.S. Pat. No. 6,699,908 (Bupivacaine in a controlled release polymeric vehicle); U.S. Pat. Nos. 6,534,081 (6,521,259) (6,514, 516) (Bupivacaine in a controlled release polymeric vehicle and augmenting agent); U.S. Pat. No. 6,217,911 (Sustained release lidocaine with capped and uncapped PLGA); U.S.

Pat. No. 6,086,863 (Microspheres non-biodegradable charged, insoluble in carrier plus pharmaceutical agent); U.S. Pat. No. 5,810,786 (Lidocaine in thermoplastic resin (not PLGA)); U.S. Pat. No. 5,292,512 (Microspheres of PLGA with active ingredient of 3-10 mgs); 2005/0002996 (Cellulose impregnated with drug, coated with polymer or fatty acid); and 2004/0076671 (Lidocaine in carrier applied to wound, also includes an antibiotic and wax matrix).

Examples of patents and patent applications that use adjuvants to enhance effectiveness include U.S. Pat. No. 7,166,641 (Diclofenac salt of lidocaine, pain relief of wounds); U.S. Pat. No. 6,645,521 (Surgically closed wounds treated with any anesthetic with oleic acid as penetration enhancer); U.S. Pat. No. 6,495,602 (Urea-includes lidocaine and acceptable salt; enhances efficacy of lidocaine); U.S. Pat. No. 6,429,228 (Lidocaine, alkanol of 2-3 carbon atoms and 8-18 carbon carboxylic acid as penetration enhancer); U.S. Pat. No. 6,426,339 (Glucocorticosteroids to extend local anesthesia); U.S. Pat. No. 6,255,502 (Lidocaine-bile acid salt for transdermal treatment); U.S. Pat. No. 6,238,702 (Local anesthetic in biodegradable controlled release with glucosteroid); U.S. Pat. No. 5,912,271 (Analgesic and polar lipid, e.g. sphingolipid); U.S. Pat. No. 5,814,659 (Topical analgesic, alcohol, chaotropic agent (e.g. urea), unsaturated fatty acid); U.S. Pat. No. 5,635,205 (Anesthetic composition with triglycerides and amphipathic ligand, e.g. phospholipid); U.S. Pat. No. 3,949,071 (Burn treatment, aqueous buffer pH 8-10, base, surface active agent, fatty acid and lidocaine); 2006/0280801 (Analgesic, fatty acid metal salts and other components); 2006/0222687 (Topical anesthetic formulation includes lidocaine and fatty acids as penetration enhancers); 2004/0228884 (Ion pair composition releases active ingredient); 2004/0214215 (Molecular complex of alkaline drug and related acid); 2004/0058994 (Surgical wounds treated with lidocaine free base or salt, includes some carboxylic acids as exemplary); and 2003/0027833 (Anesthetics (includes lidocaine) and penetration enhancers (fatty acids)). (All of these references are incorporated herein by reference to the extent that the references describe methods of preparation of salts and use of the anesthetics.)

While not specifically directed to anesthetics, an extensive patent effort has been directed by Idexx Laboratories toward the use of fatty acid salts of amine drugs as slow release compositions. Idexx Laboratories have filed U.S. Pat. Nos. 7,033,599; 6,946,137; 6,887,487; 2007/0141162; and 2005/0075296, disclosing bupivacaine as one of the drugs.

The rapid loss of anesthetic effect is shown in the following table. (emedicine.com/ent/topic20.htm; eMedicine Specialties>Otolaryngology and Facial Plastic Surgery>PHARMACOLOGY). To extend the anesthetic effect, epinephrine is employed for vasoconstriction. The data demonstrate the need and desirability to provide an increased duration for the anesthesia.

| | Onset | Maximum Dose (with Epinephrine) | Duration (with Epinephrine) |
|---|---|---|---|
| Lidocaine | Rapid | 4.5 mg/kg (7 mg/kg) | 120 min (240 min) |
| Mepivacaine | Rapid | 5 mg/kg (7 mg/kg) | 180 min (360 min) |
| Bupivacaine | Slow | 2.5 mg/kg (3 mg/kg) | 4 hours (8 h) |
| Ropivacaine | Medium | 2-3 mg/kg | 3 hours (6 h) |
| Levobupivacaine | Medium | 2.0 mg/kg or 400 mg in 24 hrs | 4-6 hours (8-12 h) |
| Procaine | Slow | 8 mg/kg (10 mg/kg) | 45 min (90 min) |
| Chloroprocaine | Rapid | 10 mg/kg (15 mg/kg) | 30 min (90 min) |
| Etidocaine | Rapid | 2.5 mg/kg (4 mg/kg) | 4 hours (8 h) |
| Prilocaine | Medium | 5 mg/kg (7.5 mg/kg) | 90 min (360 min) |
| Tetracaine | Slow | 1.5 mg/kg (2.5 mg/kg) | 3 hours (10 h) |

As evidenced from the above, there have been extensive efforts to provide anesthetics with improved properties. The efforts have entailed the use of numerous polymeric matrices to provide for extended activity of the anesthetic due to the relatively short period that the anesthetics are effective. Alternatively, other investigations have been directed to additives that will enhance the effectiveness of the anesthetics in a variety of contexts. For treatment of wounds, particularly associated with surgery or other disruption of the skin resulting in severe pain, there is a need for a simple, safe and effective anesthetic that is long lasting and can easily be administered and produced.

SUMMARY OF THE INVENTION

Aminoacid amides and esters of the "caine" family of local anesthetics are provided in particle form as salts of organic acids, particularly in a surgical setting. The subject compositions can be in powder, gel, gaseous dispersion or liquid form with intact particles and applied to the exposed tissue, such as surgically exposed, or to the skin in the case of laparoscopy. The particles are designed to provide for enhanced performance of the anesthetic, including extended release of the anesthetic over a prolonged period of time, particularly during the period of pain, for maintaining the anesthetic in the area of interest, and minimizing toxicity.

Accordingly, in one embodiment, the invention is directed to a method for improving the alleviation of pain of a surgical wound of a mammal. The method comprises administering to the area of the surgical wound a therapeutically effective amount of particles of an organic acid salt of a caine anesthetic, wherein the organic acid is at least 6 carbon atoms, whereby the anesthetic provides improved alleviation of pain.

In certain embodiments, the anesthetic is selected from the group consisting of ropivacaine, bupivacaine and lidocaine.

In additional embodiments, the organic acid is an aliphatic organic acid or an aromatic organic acid and the particles comprise up to 50% equivalent excess of the organic acid.

In yet additional embodiments, the caine is an amino acid amide or an amino acid ester.

In further embodiments, the particles are introduced into the bed of the wound, such as, but not limited to, by spraying into the bed. In certain embodiments, the particles are sprayed as an aerosol.

In additional embodiments, the particles are administered topically in a gel or liquid medium.

In yet a further embodiment, the invention is directed to a method for improving the alleviation of pain of a surgically created wound of a human. The method comprises administering particles of an aliphatic acid salt of a caine to the bed of the wound, wherein the aliphatic acid is of from 6 to 30 carbon atoms, and is present in not more than 50% equivalent excess, and the particles have a median size range in the range of about 50 to 2000 μm, whereby the caine is released from the salt over at least one day at a therapeutically effective amount and alleviates the pain.

In certain embodiments, the particles are sprayed into the bed of the wound, such as but not limited to a method wherein the particles are mixed with a propellant. In additional embodiments, the particles are dispersed in a vehicle to form a dispersion.

In further embodiments, the particles are sprayed by means of a pump.

In yet additional embodiments, the particles are in a size range of about 100 to 1200 μm.

In certain embodiments of the methods above, the particles are painted in the area of the wound.

In an additional embodiment, the invention is directed to a for alleviating pain of a surgically created wound of a human. The method comprises topically administering to the skin in proximity to the wound particles of an aliphatic organic acid salt of a caine selected from the group consisting of ropivocaine, bupivacaine or lidocaine, wherein the aliphatic organic acid is of from 6 to 30 carbon atoms and the particles are of median size in the range of 100 to 1200 μm, whereby the caine is released from the salt and transported transdermally over at least one day at a therapeutically effective amount and alleviates the pain.

These and other embodiments of the subject invention will readily occur to those of skill in the art in view of the disclosure herein.

DESCRIPTION OF THE SPECIFIC EMBODIMENTS

Figure 1:
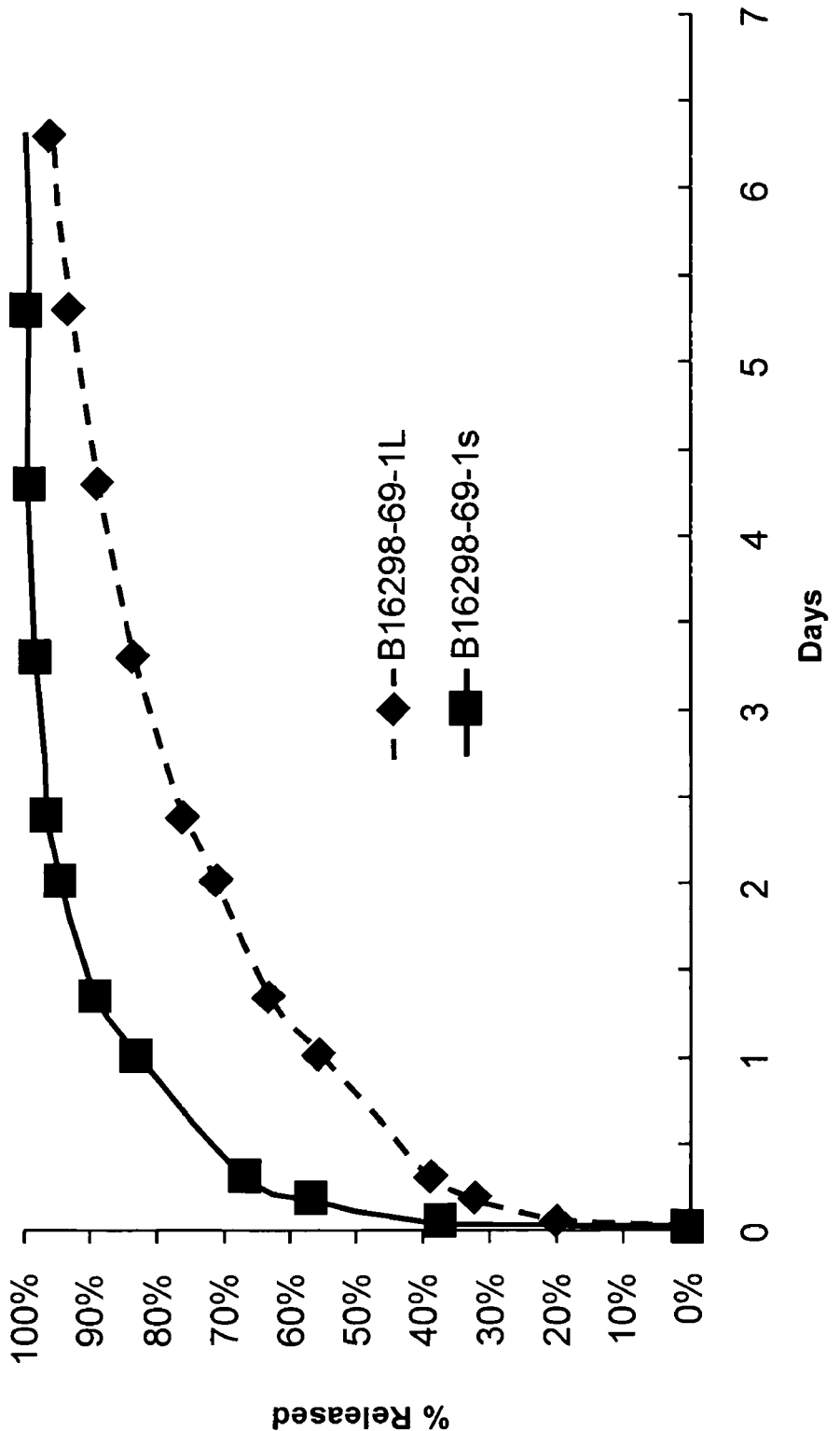
FIG. 1 is a graph of the release of the lidocaine over time for the large particle formulation referred to as B16 298-69-1L and the small particle formulation referred to as B16 298-69-1s.
Figure 2A:
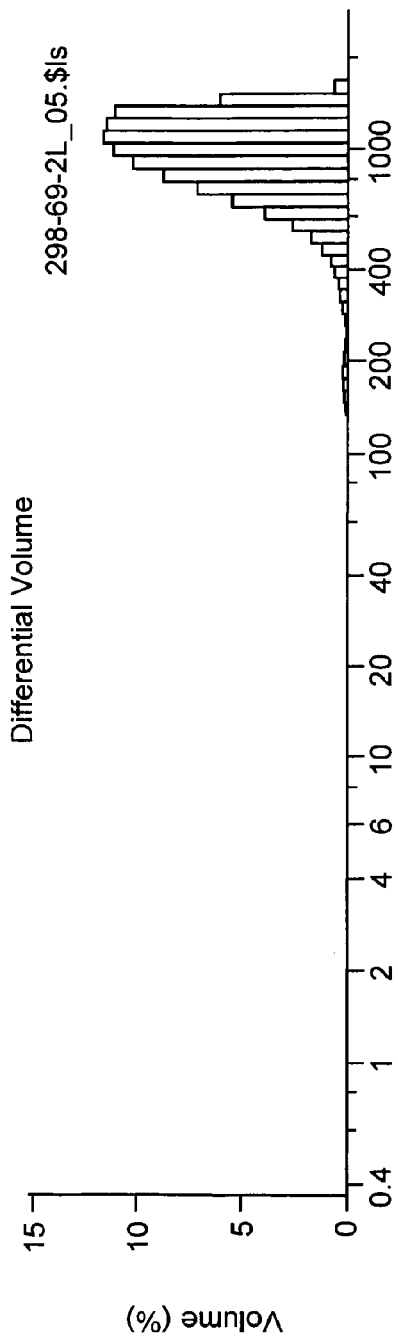
FIGS. 2A-2B show the size distribution of the large particles (FIG. 2A) and the small particles (FIG. 2B) in the formulation.
Figure 2B:
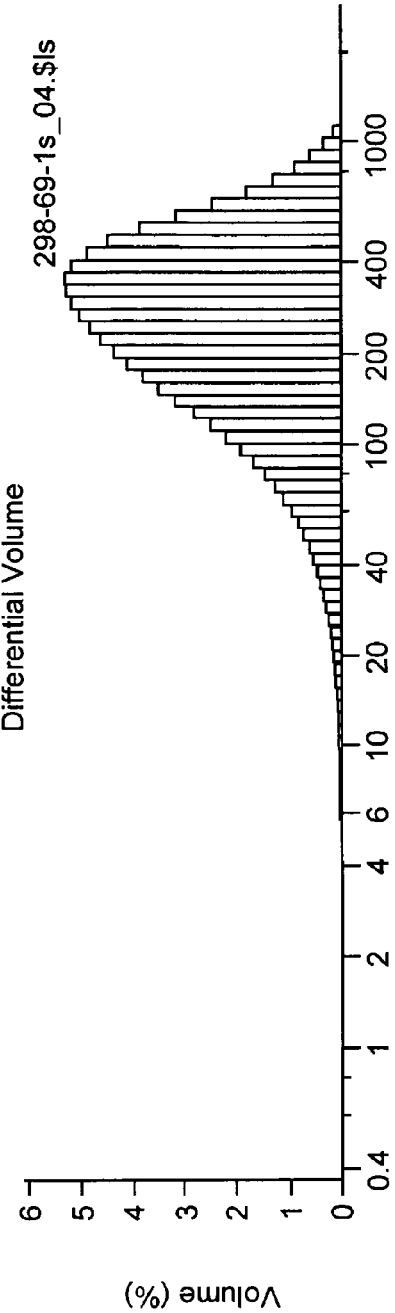
Figure 3:
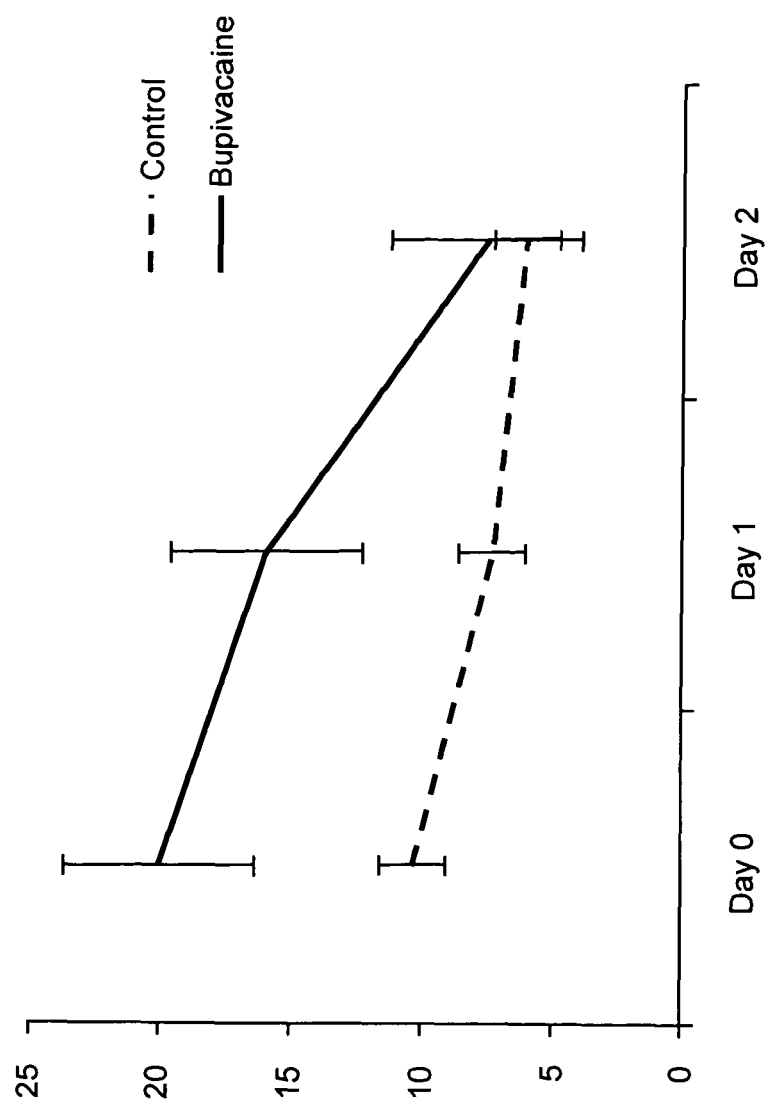
FIG. 3 is a graph of the results of a rat test for time to respond with and without treatment with the bupivacine-palmitate particles.

In accordance with the subject invention anesthetic particles are provided for the treatment of pain causing injury, particularly wounds, where the particles comprise as their major ingredient an organic acid salt of an amino acid amide or ester local anesthetic. Examples of the amino acid amide and ester local anesthetics have been indicated above, where of particular interest are lidocaine, bupivacaine and ropivacaine. The organic acid salt will form an ionic species that is substantially neutral and hydrophobic, while the individual components are charged and capable of solvation and being separated at physiological pH.

The organic acid salts include pharmacologically acceptable acids that for the most part will be carboxylic acids, particularly aliphatic and sulphonic acids, where the organic acid is of at least about 6, usually at least about 8, carbon atoms, and the like. The aliphatic carboxylic acids that form the salts of particular interest will usually be from about 6 to 30 carbon atoms, more usually 6 to 24, frequently 8 to 24, particularly 12 to 24 carbon atoms. These acids may be aliphatically saturated or unsaturated, usually having no more than three sites of unsaturation, particularly ethylenic, and will be for the most part be even numbered. Illustrative carboxylic acids include capric, caproic, caprylic, lauric, myristic, palmitic, stearic, oleic, linoleic, linolenic, arachadonic and the like and for the most part are selected as being designated as GRAS (generally regarded as safe). The aliphatic acids may be substituted or unsubstituted, but will retain low water solubility, generally being less than about 5 weight % soluble at 25° C. Generally, substituents will include hydroxyl, halo, etc. The sulfonic acids include such acids as benzene sulfonic acid and its derivatives, N-2-hydroxyethyl piperazine-N-2-ethane sulfonic acid, naphthalenesulfonic acid and derivatives thereof, octane-2-sulfonic acid and derivatives thereof, toluene sulfonic acid and derivatives thereofhe salt composition may have a 1:1 equivalent ratio of the anesthetic to the carboxylic acid or one of the components may be in excess, usually not more than about 5-fold excess, generally up to about 0.5, or up to about a 0.2, equivalent excess of either of the components of the salt may be present. By having excess carboxylic acid, the release rate of the caine from the salt may be diminished by virtue of the common ion effect, where the dissolution of the excess carboxylic acid will act to slow or retard the dissolution rate of the caine salt compound in the particles The size distribution of a particle composition will generally have at least about 50 weight % within 75%, more usually within 50%, and desirably within 25% of the median size. The median size will generally range from about 50 to about 2000 μm, more usually from about 50 to 1500 μm, desirably from about 100 μm to 1200 μm. Individual compositions of interest have median sizes of about 100 to 200 μm, 300 to 500 μm and 750 to 1200 μm.

The particles may have a single salt or have a mixture of salts, where a single particle may be a mixture or the composition may be a mixture of particles of different salts. By using different acids, the rate of release of the anesthetic can be modulated, the smaller carbon acids usually providing for more rapid release. The composition may be a mixture of different sized particles, usually comprising not more than two different distributions, where each of the different distributions has at least about 75% of the weight of the particles within 50%, more usually within 25%, of the median weight. The median weights of the two differently sized compositions will usually differ by at least about 25%, more usually at least about 50% and there may be a two-fold difference or greater. In this way both composition and particle size can be varied to provide the optimum release profile for the particular application for the subject compositions.

Depending upon the manner in which the particles are made, there may be less than about 2, more usually less than about 1, weight % of the solvent used in their preparation, and preferably undetectable amounts.

In treating the wound the particles may be administered directly into the wound bed and onto the tissue for an open wound or onro the raw surface in case of laparoscopy or other minimally invasive procedure. The particles may be administered by spraying, coating, painting, injecting, irrigating, adhered to a substrate, which substrate is placed in the wound, or the like. Spraying may be employed for administration of the particles with or without a vehicle, using a pharmacologically acceptable propellant. Air may be pumped to disseminate the particles.

Suitable topical vehicles, vehicles for aerosols and other components for use with the formulations of the present invention are well known in the art. These vehicles may contain a number of different ingredients depending upon the nature of the vehicle, the nature of the wound, the manner of administration, and the like. The vehicles will provide for a convenient method of administration to the wound, while not adversely affecting the controlled release of the anesthetic from the particles.

Most common propellants are mixtures of volatile hydrocarbons, typically propane, n-butane and isobutane, or hydrofluoroalkanes (HFA): either HFA 134a (1,1,1,2,-tetrafluoroethane) or HFA 227 (1,1,1,2,3,3,3-heptafluoropropane) or combinations of the two or compressed gases such as nitrogen, carbon dioxide, air and the like. One may also use a simple air brush means of dispensing the particles where there is literally no solvent but air is drawn and used to dispense the particles.

Liquid media used for dispersing the particles should be highly volatile or miscible with the aqueous environment of the wound and rapidly evaporate or dissipate under the conditions of administration. The liquids will for the most part be non-solvents for the anesthetic salt, although there may be minimal solubility. Such vehicles may include non-solvent liquid media that include water, mixtures of water and organic solvents and mixtures of organic solvents. Other additives may include protein-based materials such as collagen and gelatin; silicone-based materials; stabilizing and suspending agents; emulsifying agents; and other vehicle components that are suitable for administration to the skin, as well as mixtures of these components and those otherwise known in the art. The vehicle can further include components adapted to improve the stability or effectiveness of the applied formulation, such as preservatives, antioxidants, and skin penetration enhancers. Examples of such components are described in the following reference works hereby incorporated by reference: Martindale—The Extra Pharmacopoeia (Pharmaceutical Press, London 1993) and Martin (ed.), Remington's Pharmaceutical Sciences.

The choice of a suitable vehicle will depend on the particular physical form and mode of delivery that the formulation is to achieve. Examples of suitable forms include liquids; solids and semisolids such as gels, foams, pastes, creams, ointments, powders and the like; colloidal drug delivery systems, for example, liposomes, microemulsions, microparticles, or other forms.

The topical formulations of the present invention can be prepared in a variety of physical forms. For example, solid particles, pastes, creams, lotions, gels, and liquids are all contemplated by the present invention. A difference between these forms is their physical appearance and viscosity, which can be governed by the presence and amount of emulsifiers and viscosity adjusters present in the formulation. Particular topical formulations can often be prepared in a variety of these forms. Solids are generally firm and will usually be in particulate form; solids optionally can contain liquids, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams may also contain liquids, emulsifiers, moisturizers, emollients, fragrances, dyes/colorants, preservatives and other ingredients that increase or enhance the efficacy of the final product. Liquids are thinner than creams, lotions, or gels and often do not contain emulsifiers.

Suitable emulsifiers for use in the formulations of the present invention include, but are not limited to ionic emulsifiers, behentirmonium methosulfate, cetearyl alcohol, non-ionic emulsifiers like polyoxyethylene oleyl ether, PEG-40 sterate, ceteareth-12, ceteareth-20, ceteareth-30, ceteareth alcohol, PEG-100 stearate, glyceryl stearate, or combinations or mixtures thereof.

Suitable viscosity adjusting agents for use in the formulations of the present invention include, but are not limited to protective colloids or non-ionic gums such as hydroxyethylcellulose, xanthan gum, magnesium aluminum silicate, silica, microcrystalline wax, beeswax, paraffin, and cetyl palmitate, or combinations or mixtures thereof.

Suitable liquids for use in the formulations of the present invention will be selected to be non-irritating and include, but are not limited to water, propylene glycol, polyethylene glycols, polypropylene glycols and mixtures thereof. Not more than about 10 weight %, usually not more than 5 weight %, of the anesthetic salt will be soluble in the medium; preferably the anesthetic salt will be insoluble in the medium.

Suitable surfactants for use in the formulations of the present invention include, but are not limited to nonionic surfactants. For example, dimethicone copolyol, polysorbate 20, polysorbate 40, polysorbate 60, polysorbate 80, lauramide DEA, cocamide DEA, and cocamide MEA, are contemplated for use with the formulations of the present invention. In addition, combinations or mixtures of these surfactants can be used in the formulations of the present invention.

Suitable preservatives for use in the formulations of the present invention include, but are not limited to antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. In addition, combinations or mixtures of these preservatives can be used in the formulations of the present invention.

Suitable moisturizers for use in the formulations of the present invention include, but are not limited to lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. In addition, combinations or mixtures of these moisturizers and emollients can be used in the formulations of the present invention.

Other suitable additional ingredients that may be included in the formulation of the present invention include, but are not limited to, abrasives, absorbents, anticaking agents, anti-foaming agents, anti-static agents, astringents, binders/excipients, buffering agents, chelating agents, film forming agents, conditioning agents, opacifying agents, pH adjusters and protectants. Examples of each of these ingredients in topical product formulations, can be found in publications by The Cosmetic, Toiletry, and Fragrance Association (CTFA). See, e.g., CTFA Cosmetic Ingredient Handbook, 2.sup.nd edition, eds. John A. Wenninger and G. N. McEwen, Jr. (CTFA, 1992).

In many instances it may be desirable that the health care professional administering the particle formulation is able to insure uniform coverage or otherwise be able to see what areas have been covered and how extensively the particle formulation has been distributed. Therefore, one may include a detectable composition with the particles so that they can be visualized. This may include colored compounds or dyes, fluorescent compounds and even luminescent compounds.

The dyes should be highly colored and visible in the presence of blood, while the fluorescent compounds should fluoresce under ultra-violet light. See, for example, Richard P. Haugland; Molecular Probes—Handbook of Fluorescent Probes and Research Chemicals; 5th Edition 1992-94; Molecular Probes, Inc.

The particles will be at least about 1 weight %, usually at least 2 weight %, and up to 100 weight % of the non-volatile portion of the composition. Where the particles are dispersed in a vehicle, the weight % of the particles will generally be in the range of about 1-75 weight %, more usually about 1-50 weight %. The minor ingredients except for the medium will generally range from about 0.01 weight % to about 10 weight %, the amount generally being conventional for the purpose of the ingredient. Where the particles are sprayed as an aerosol, generally the particles will be present in the range of about 1 to 99 weight % of the composition.

Depending upon the need and the nature of the composition, the composition may be sprayed, wiped, smeared, painted, transferred from a template onto or proximal to the wound or may be made into a patch where the composition will be separate from or part of the adhesive. Alternatively, topically the composition may be applied to the wound and a dressing or other protective layer added to prevent contamination and abrasion. In some situations the composition may be injected, particularly where a minimally invasive surgical technique is employed and the rate of transdermal transport is insufficient to provide the pain relief required. Not more than one application should be required per 6 hours, usually per half-day, and times between applications may vary from 6 hours to 7 days, usually 12 hours to 4 days, where frequently by 7 days further treatment will not be required. During this time a therapeutically effective amount of the caine will be released from the particles.

The amount of the anesthetic salt applied to the wound area will be a therapeutically effective amount to minimize pain to a level that the patient can tolerate and preferably substantially eliminate any sense of pain. The amount of pain will usually vary with time, so that the amount of anesthetic that will be required can be diminished over time. Therefore, the profile of anesthetic release from the salt can be a diminishing amount of anesthetic being released over time. Conveniently, there may be an initial large release, less than about 30%, usually less than about 25%, of the total amount of anesthetic followed by a decreasing release over time at a lower amount at a therapeutic level. The large initial release coincides with the high levels of pain in the early post-operative period. After the initial release, generally not more than 60 weight %, more usually not more than about 50 weight %, will be released in 24 hours, where the pain alleviation is to occur over generally greater than two days, with diminishing percentages as the time for relief is extended.

The subject treatment may be used with ancillary treatments, such as an initial conventional anesthetic administration prior to or concurrent with the application of the subject composition.

While for the most part the patient will be human, any mammal that has been injured or undergone surgery can enjoy the benefits of the anesthetic salt. Therefore, included as patients are domestic animals, e.g. horses, dogs, cats; wild animals, particularly wild animals found in zoos, and the like.

The subject compositions can be prepared in accordance with known techniques. The anesthetic base and organic acid can be brought together in an appropriate medium where the two components are dissolved and form the salt. Dissolution may be a result of a temperature increase, generally a temperature below about 60° C., where cooling results in precipitation of the salt. Alternatively, a solvent can be used in which the components are soluble, but the salt is not, so that the salt precipitates upon formation. Another technique is to add a non-solvent that results in the precipitation of the salt, where the salt is the least soluble of the three components in the solution. Another technique is to remove the solvent that allows for the dissolution of the anesthetic base, the organic acid and the resulting salt. Another technique is to combine the anesthetic base and organic acid in the molten state to allow reaction to occur. There are numerous other approaches that may also be used to prepare such salts that are known to those skilled in the art.

The precipitate is then isolated and may be treated in a variety of ways to achieve the desired size composition. The precipitate may be ground and then the particles size selected, dissolved in a volatile solvent and sprayed from a nozzle into a vacuum where the solvent evaporates leaving particles of the desired size, dissolved in an appropriate solvent and precipitated in a non-solvent in a manner know to those skilled in the art to prepare microparticles or other conventional technique. Where other ingredients are included in the particle, these ingredients may be included in the solvent used to spray the solution of the salt, or in the precipitation method, etc. Where anticaking or antiagglomeration is necessary, the particles can be blended with an appropriate agent, such as talc, sodium bicarbonate, magnesium carbonate, etc.

The particles are then packaged and stored at room or lower temperature or are mixed with a propellant and, as appropriate, a vehicle, and stored in a pressure container. Instead, a pump bottle may be used where only a vehicle would be required. Alternatively, the particles may be kept separate from the vehicle and combined with the vehicle shortly prior to or at time of administration. In some cases it may be desirable to compound the caine salt with an amount of the organic acid itself to also help control the release rate of the caine in the intended application using the common ion effect to affect the dissolution of the salt. For example, a drug product can be prepared containing 50% of the organic acid caine salt and 50% of the organic acid. The amount of added organic acid to the composition will be determined by calculation to provide the desired composition for the release rate and profile. The above drug product preparation routes may be equally applied for the preparation of microparticles that contain both the organic acid caine salt and the organic acid.

Once the particles have been prepared, irrespective of the method employed in their preparation, the particles are sized and fractioned typically by sieving operations, although other methods may be employed. To control particle distribution and particle size a typical sieving operation would employ at least 2 sieves of the appropriate size. The larger sieve size would allow for the rejection of particles larger then the specified maximum while the lower sieve size would serve to retain the particles of the specified size. The selection of the sieves determines the particle size distribution. Using this approach one can also prepare multimodal distributions to obtain different release profiles of drug. Nominal particle size and particle size distribution is determined by an instrument such as a Coulter LS13 on suspensions of the microparticles.

Drug dissolution kinetics is evaluated using an LC method employing an infinite sink concept. A known amount of microparticles are suspended in a defined volume of a suitable test medium, for example a phosphate buffer solution containing 1% Tween 80, meant to simulate in vivo release kinetics. The suspension of microparticles is kept at a constant temperature, typically 37° C. for a period of time, for example, about 12 hours, with constant agitation. The particles are removed from the solution by filtration and resuspended in another fresh amount of the test media. The original solution is assayed for the amount of drug product in solution by an appropriate quantitative method, typically an LC method employing UV detection or MS.

If fluorescent or colored microparticles are desired the procedure for making the microparticle is followed, however, for a fluorescent product a compound such as fluorescein is added to the mixture before the precipitation or preparation of the microparticle is attempted. If a colored product is required a food safe dye such as FD&C Blue No 1 or Blue No 2 is used.

Drug product of the appropriate size is combined with other agents that may be appropriate to provide free flowing stable microparticles and added to an appropriate aerosol container. The aerosol container is subsequently pressurized with a high purity propellant and sealed under pressure with the appropriate spray nozzle to provide the spray pattern desired and in some cases to provide a metered dose of the drug. Alternatively the drug product can be suspended into a PBS solution or other suitable vehicle just prior to application to the wound. The product is distributed over the wound by spraying using a variety of possible propulsion systems e.g. an air brush type of system, pump sprayer system, etc., whereby drug product suspended in the PBS is aspirated through a tube using the Venturi concept with a propellant container. The amount dispensed per unit time and spray pattern are determined by the nozzle selected at the time of application by the health care professional.

The following examples are offered by way of illustration and not by way of limitation.

EXPERIMENTAL

A general procedure is provided for any of the members of the caine family.

The caine as the hydrochloride salt is dissolved in a suitable organic solvent such as chloroform that dissolves both the hydrochloride form as well as the free base. The hydrochloride salt is neutralized by addition of a stoichiometric amount of triethyl amine producing the free base of the caine. Alternatively the synthesis is started using the commercially obtained free base form of the caine. Alternatively the hydrochloride salt is dissolved into water and a stoichiometric amount of sodium hydroxide is added dropwise with stirring. The free base form of the caine is essentially insoluble in water and precipitates during the course of the addition of the strong base. Alternatively the free base may be extracted from the aqueous phase using a solvent that is immiscible with water and dissolves the free base caine, using such solvents as chloroform, methylene chloride, diethyl ether and the like providing such properties.

A solution of the free base of the appropriate caine is treated with a stoichiometric amount of a solution of the carboxylic acid in a solvent that completely dissolves both the free base form of the caine and the carboxylic acid. Solvents such as alcohols or chlorinated solvents are employed. The solution is heated for varying times depending upon the caine and carboxylic acid chosen until the reaction is complete and the product isolated either by precipitation into a non-solvent or by evaporating the solvent to dryness and isolating the product as a dry solid.

The dry solid is recrystallized to remove any unreacted carboxylic acid by dissolving the product in 2-propanol and adding water to the solution to cause crystallization of the product. Other solvents such as N-methyl pyrrolidone (NMP), tetrahrydofuran (THF), acetonitrile (ACN) and other organic water miscible solvents are suitable for this purpose. The product may be recyrstallized from 1 to 2 times depending upon the purity of the compound that is desired. Purification by chromatographic techniques such as reverse phase chromatography is performed by dissolving the product in acetonitrile and applying the solution to C18 modified silica, and eluted using a mobile phase with an isocratic or gradient eluent. If desired, the compound may be purified by simple precipitation of the dissolved product in diethyl ether, which preferentially precipitates the caine salt but allows for the solubility of the fatty acid.

The purified fatty acid salt of the caine is converted to microparticles of known size and size distribution through the process of controlled precipitation. A solution of the drug is prepared in ethyl acetate and filtered to remove undissolved particulates. The solution is added slowly with vigorous stirring to aqueous methanol, a nonsolvent for the drug but one miscible with the ethyl acetate, causing controlled precipitation of the microparticles. Polyvinyl alcohol is conveniently employed to allow for the generation of particles that do not adhere to one another.

Alternatively the microparticles are prepared by dissolving the drug product into an aqueous immiscible solvent such as methylene chloride. This solution is added with vigorous agitation to a methylene chloride pre-saturated aqueous solution containing a surfactant such as polyvinyl alcohol. The drug product separates as insoluble particles that are subsequently filtered from the medium and dried to remove traces of solvent.

Alternatively the drug product is dissolved in methylene chloride. The solution is sprayed through an appropriately sized nozzle at predetermined rates into a heated and/or vacuum chamber allowing for the rapid volatilization of the solvent leaving the insoluble drug product microparticles. The appropriate nozzle size, temperature and drying conditions are known to those skilled in the art.

The salt bupivacaine palmitate was prepared by dissolving 18.3% w/v bupivacaine free base and 16.7% w/v palmitic acid.

| Diethyl ether 3 ml | |
|---|---|
| Material | Amount |
| Bupivacaine Free Base | 549.9 mg |
| Palmitic Acid | 501.5 mg |

These materials were dissolved by vortexing at room temperature. Without waiting for a significant period of time, the mixing vessel was left open under laminar flow for 3 days to evaporate ether. The vessel was then placed under vacuum at room temperature at −25 psig for 24 hours. Bupivacaine palmitate was removed from the vessel in large pieces after drying. Using a sharp blade, bupivacaine palmitate particles were formed by repeated chopping until the desired size range was achieved. Bupivacaine palmitate particles were size separated by collection over a 500 μm sieve. Particle size analysis confirmed a mean particle size of approximately 940 μm, and differential scanning calorimetry confirmed absence of bupivacaine and palm itic acid peaks with concomitant appearance of a new peak. The particles that passed through the sieve had a mean particle size of approximately 340 μm. The solubility profile for the two fractions is shown in FIG. 1.

Particle size characteristics of bupivacaine palmitate particles were determined using a Coulter LS13230 static light scattering instrument. A mass of 100 mg of particles was suspended in 2 ml of 0.1% Tween 80 in water. The micro-volume module attachment was filled with deionized water.

The stir speed was set at 32%, and alignment and background corrections were performed. Using a transfer pipette, particle suspension was added to the micro-volume cell until obscuration was between 8 and 12%. Particle size data collection was performed for 60 seconds, and particle size was estimated using the Fraunhofer approximation.

The particles were irradiated with a sterilizing dose of gamma-radiation. No change was observed in the nature or the in vitro release kinetics of the particles.

In vitro release of particles was determined as follows: An exact mass of approximately 10 mg was weighed into a 15 ml glass test tube (Fisherbrand Disposable culture tubes, P/N: 14-957-16A). A volume of 5 ml of phosphate buffered saline (PBS) (Hyclone, P/N: SH30256.02) was added to each test tube. A serum separator filter (Fisher, P/N: 02-681-63) was placed in each test tube and capped with a serum filter cap (Fisher, P/N: 02-681-63). Capped tubes were then placed upright in a Thermo Precision Reciprocal Shaking Water Bath (P/N: 51121081) at 37° C. shaking at 120 rpm. At approximately 1, 4, and 9 hours on the first day, the serum filter was used to remove all but approximately 0.2 ml supernatant. A portion of the supernatant was collected for analysis and the remaining amount was discarded. A new volume of 5 ml of PBS was added to the test tube, and the same serum filter was replaced. After the first day, release samples were collected once or twice for a period of approximately 9 days. Collected samples were stored refrigerated until analyzed.

Analysis of bupivacaine salts and their release characteristics was performed using a reverse phase HPLC method with a ultraviolet/visible spectrophotometer (UV/Vis) detector for the detection of the caine and an ELSD (evaporative light scattering) detector for the organic acid component. A typical experimental setup consists of the following instrumental components: Waters 1525 Binary Pump, Waters 2487 Dual Wavelength Absorbance Detector, Waters 717plus Autosampler and Alltech ELSD 2000. Ambient temperature was used with the autosampler and a Phenomenex Gemini C18 110A (150 mm length, 4.6 mm i.d., 3 µm packing) was used also at ambient temperature. The flow rate was adjusted to 1 ml/min with a isocratic mobile phase consisting of a binary mixture comprised of 45% of 0.1% triethanol amine (TEA) in water at a pH 10 and 55% acetonitrile (ACN). UV detection was performed at 220 nm and the ELSD detector was set to 80° C. with a nebulizer flow of 1.5 L/min. An injection volume of 25 µl was used. Typical runs times were 20 minutes. System calibration was performed using pure bone fide bupivacaine and palmitic acid components.

The next study was an in vivo study.

To test the local anesthetic efficacy and duration of effect induced by bupivacaine palmitate particles, a treatment and control side in a male, Sprague-Dawley rat (250-300 g) was employed. The animal was anesthetized with isoflurane inhalation (2.5-3%), whereupon the back was partly shaved. A 16 g needle was introduced deep to the shaved skin on the left mid paraspinal back and moved side to side to clear a small (1.0 cm diameter) pocket. A similar procedure was performed on the right side. The needle was then used to introduce test local anesthetic bupivacaine palmitate particles into the pocket on the right side.

The rat was awakened and placed in a Decapicone for restraint. As restraint itself can produce endogenous analgesic effects, the animal was allowed to rest quietly in the cone for 15 min prior to any testing. Radiant heat from a focused projection bulb with area of approximately 0.5 cm² was then directed to the test areas to assess the pain threshold several times on each side. The light was applied until the rat attempted to move within the restraint cone, at which time the light heat stimulus was turned off. The light heat stimulus was never allowed to exceed a 20 seconds interval in order to avoid permanent damage to the skin or undue discomfort.

The post-procedural results at 15 min, 1 and 2 days are represented in average number of seconds before movement:

|  | Control | Bupivacaine |
|---|---|---|
| Day 0 | 10.3 | >20 |
| Day 1 | 7.366667 | 16 |
| Day 2 | 6.125 | 7.6 |

The subject invention provides a substantial advance over present compositions and procedures for alleviating pain, particularly during and after surgical procedures. The compositions of the subject invention are formulated for ease of use by the surgeon and efficacy over an extended period of time. The subject compositions are particularly suitable for introduction into the wound bed. After closing the wound, the subject particles will continue to release an effective amount of the anesthetic for a prolonged period, alleviating the pain and diminishing or obviating the need for systemic pain killers. The components are safe and will readily be metabolized by the body leaving no residue. The compositions have low, if any, toxicity and can provide for enhanced localization of the anesthetic. The subject compositions are easily prepared, handled and formulated to provide the desired anesthetic activity. The formulations can provide for transdermal transport of the anesthetic to provide anesthetic effect at the site of injury.

Although the invention has been described with reference to the above examples, it will be understood that modifications and variations are encompassed within the spirit and scope of the invention. Accordingly, the invention is limited only by the following claims. All references referred to in the specification are hereby incorporated by reference as if fully set forth herein.

What is claimed is:

1. A method for alleviating pain associated with a surgical wound of a mammal, said method comprising:
    administering to the area of said surgical wound a therapeutically effective amount of particles consisting essentially of (a) an organic acid salt of a caine anesthetic or (b) an organic acid salt of a caine anesthetic and the organic acid, wherein the organic acid has at least 6 carbon atoms, provided that said particles do not comprise a polymeric matrix or a wax matrix which controls the release of the caine anesthetic, and wherein the particles are of median size in the range of 50 to 2000 µm; whereby said caine anesthetic is released by dissolution of said salt and provides alleviation of pain.

2. The method according to claim 1, wherein said caine anesthetic is selected from the group consisting of ropivacaine, bupivacaine and lidocaine.

3. The method according to claim 1, wherein said particles are prepared by dissolving said caine anesthetic and said organic acid in a solvent; and
    precipitating the organic acid salt of said caine anesthetic from said solvent as particles or forming particles from said precipitate.

4. A method according to claim 1, wherein said organic acid is an aliphatic organic acid and said particles comprise up to 50% equivalent excess of said aliphatic organic acid.

5. A method according to claim 1, wherein said organic acid is an aromatic organic acid and said particles comprise up to 50% equivalent excess of said aromatic organic acid.

6. A method according to claim 1, wherein said caine anesthetic is an amino acid amide.

7. A method according to claim 1, wherein said caine anesthetic is an amino acid ester.

8. The method according to claim 1, wherein said particles are introduced into the bed of said wound.

9. The method according to claim 8, wherein said particles are sprayed into said bed.

10. The method according to claim 1, wherein said particles are administered topically in a gel or liquid medium.

11. A method for alleviating pain associated with a surgically created wound of a human, said method comprising:
   administering particles consisting essentially of an organic acid and a caine anesthetic, to the bed of said wound, wherein said organic acid is of from 6 to 30 carbon atoms, provided that said particles do not comprise a polymeric matrix or a wax matrix which controls the release of the caine anesthetic, and wherein the particles are of median size in the range of 50 to 2000 µm;
   whereby said caine anesthetic is released by dissolution of said salt and alleviates said pain.

12. A method according to claim 11, wherein said particles are sprayed into the bed of said wound.

13. A method according to claim 12, wherein said particles are dispersed in a vehicle to form a dispersion.

14. A method according to claim 10, wherein said particles are painted in the area of said wound.

15. A method for alleviating pain associated with a surgically created wound of a human said method comprising:
   topically administering to the skin in proximity to said wound particles consisting essentially of an aliphatic organic acid salt of a caine selected from the group consisting of ropivicaine, bupivicaine or lidocaine and 0 to 50% equivalent excess of the aliphatic organic acid, wherein said aliphatic organic acid is of from 6 to 30 carbon atoms and said particles are of median size in the range of 100 to 1200 µm, provided that said particles do not comprise a polymeric matrix of a wax matrix which controls the release of the caine anesthetic;
   whereby said caine is released by dissolution of said salt and transported dermally over at least one day at a therapeutically effective amount and alleviates said pain.

16. The method of claim 1, wherein the organic acid is a sulfonic acid.

17. The method of claim 11, wherein the organic acid is a carboxylic acid.

18. The method of claim 16, wherein the sulfonic acid is benzenesulfonic acid; N-2-hydroxyethylpiperazine-N-2-ethanesulfonic acid; naphthalene sulfonic acid; octane-2-sulfonic acid; or toluene sulfonic acid.

19. The method of claim 17, wherein the acid is an aliphatic carboxylic acid.

20. The method of claim 17, wherein the acid is an aliphatic carboxylic acid of 12 to 24 carbon atoms.

\* \* \* \* \*

UNITED STATES PATENT AND TRADEMARK OFFICE
CERTIFICATE OF CORRECTION

PATENT NO. : 8,920,843 B2  
APPLICATION NO. : 12/734520  
DATED : December 30, 2014  
INVENTOR(S) : Sawan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 263 days.

Signed and Sealed this
Twentieth Day of October, 2015

Michelle K. Lee
*Director of the United States Patent and Trademark Office*